(12) United States Patent
Rogers et al.

(10) Patent No.: US 6,709,439 B2
(45) Date of Patent: Mar. 23, 2004

(54) SLAPHAMMER TOOL

(75) Inventors: Christopher Rogers, Taunton, MA (US); Patrick Fatyol, New Bedford, MA (US); Michael Sorrenti, Middleboro, MA (US); Thomas M. DiMauro, Southboro, MA (US)

(73) Assignee: DePuy Spine, Inc., Raynham, MA (US)

( * ) Notice: Subject to any disclaimer, the term of this patent is extended or adjusted under 35 U.S.C. 154(b) by 120 days.

(21) Appl. No.: 10/021,527

(22) Filed: Oct. 30, 2001

(65) Prior Publication Data
US 2003/0083668 A1 May 1, 2003

(51) Int. Cl.⁷ ............................................. A61B 17/58
(52) U.S. Cl. .................................. 606/100; 606/86
(58) Field of Search ................ 606/100, 104, 606/99, 103, 86, 79; 433/151, 121

(56) References Cited
U.S. PATENT DOCUMENTS

| | | | |
|---|---|---|---|
| 2,421,354 A | * | 5/1947 | Reiter .......................... 606/100 |
| 2,437,014 A | * | 3/1948 | Arnesen et al. .............. 606/100 |
| 2,725,878 A | * | 12/1955 | Reiter .......................... 606/79 |
| 4,034,746 A | | 7/1977 | Williams |
| 4,300,885 A | * | 11/1981 | Khait .......................... 433/151 |
| 4,423,721 A | | 1/1984 | Otte et al. |
| 4,877,020 A | | 10/1989 | Vich |
| 4,993,410 A | | 2/1991 | Kimsey |
| 5,019,081 A | | 5/1991 | Watanabe |
| 5,052,373 A | | 10/1991 | Michelson |
| 5,078,718 A | | 1/1992 | Moll et al. |
| 5,282,804 A | | 2/1994 | Salyer |
| 5,314,477 A | | 5/1994 | Marnay |
| 5,431,658 A | | 7/1995 | Moskovich |
| 5,476,467 A | | 12/1995 | Benoist |
| 5,505,732 A | | 4/1996 | Michelson |
| 5,534,006 A | | 7/1996 | Szabo et al. |
| 5,741,253 A | | 4/1998 | Michelson |
| 5,797,909 A | | 8/1998 | Michelson |
| 5,797,917 A | | 8/1998 | Boyd et al. |
| 5,800,546 A | | 9/1998 | Marik et al. |
| 5,913,860 A | | 6/1999 | Scholl |
| 5,944,658 A | | 8/1999 | Koros et al. |
| 5,957,927 A | | 9/1999 | Magee et al. |
| 6,022,357 A | | 2/2000 | Reu et al. |
| 6,063,088 A | | 5/2000 | Winslow |
| 6,096,038 A | | 8/2000 | Michelson |
| 6,139,551 A | | 10/2000 | Michelson et al. |
| RE37,005 E | | 12/2000 | Michelson et al. |
| 6,156,040 A | | 12/2000 | Yonemura et al. |
| 6,159,212 A | | 12/2000 | Schoedinger, III et al. |
| 6,159,244 A | | 12/2000 | Suddaby |
| 6,197,033 B1 | | 3/2001 | Haid, Jr. et al. |

FOREIGN PATENT DOCUMENTS

| | | |
|---|---|---|
| DE | 2101002 | 5/1972 |
| EP | 0 780 090 A1 | 6/1997 |
| EP | 0 780 092 A1 | 6/1997 |
| EP | 0 780 906 A2 | 6/1997 |

* cited by examiner

*Primary Examiner*—Pedro Philogene
(74) *Attorney, Agent, or Firm*—Nutter McClennen & Fish LLP

(57) ABSTRACT

A medical instrument impacting tool that is useful for mating to a medical instrument used during spinal surgery is provided. The impacting tool is effective to apply a force to the medical instrument to efficiently and effectively prepare a bone structure, insert or remove a trial implant, insert or remove an implant, or to remove a medical instrument positioned between adjacent bone structures. In general, the medical instrument impacting tool includes a hollow tube, a handle slidably disposed around the tube, and a mass connected to the handle and slidably disposed within the tube.

19 Claims, 10 Drawing Sheets

SLAPHAMMER TOOL

FIELD OF THE INVENTION

The present invention relates to medical instrument insertion and removal tools, and more particularly to a medical device impacting tool adapted to apply a force to a medical device used during orthopedic surgery.

BACKGROUND OF THE INVENTION

Advancing age, as well as injuries, can lead to changes in the various bones, discs, joints and ligaments of the body. In particular, these changes can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebra. This separation is necessary for allowing both the afferent and efferent nerves to exit and enter, respectively, the spinal column.

Treatment for a diseased or damaged disc can involve the removal of the affected disc and subsequent fusion of the opposing vertebra to one another. Spinal fusion consists of fusing the adjacent vertebrae through the disc space (the space previously occupied by the spinal disc interposed between the adjacent vertebral bodies). Typically, a fusion cage and/or bone graft is placed into the disc space to position the vertebrae apart so as to create more space for the nerves, to restore the angular relationship between the adjacent vertebrae to be fused, and to provide for material that can participate in and promote the fusion process.

Several different tools have been developed to facilitate the preparation of the adjacent vertebral bodies, as well as the subsequent placement of an implant between adjacent bone structures. Typically, prior to insertion of an implant, bone preparation tools are used to prepare the bone surfaces of the adjacent vertebrae. Mallets are often used to apply an impacting force on a medical tool, such as a chisel, to remove bone from a vertebral body. Mallets are also commonly used to insert an implant, and to remove tools positioned between adjacent vertebrae. While mallets are effective, the impacting force must be axially applied to avoid misalignment of the prosthesis, or the inadvertent removal of bone. Moreover, the force applied must be sufficiently accurate to avoid damage to the vertebrae.

To overcome some of these problems, slaphammers have been developed and are widely used in orthopedic procedures to apply an impacting force on various tools used during surgery. However, most slaphammer designs still have several drawbacks. Current slaphammers tend to be very large and heavy, and are thus difficult to handle. Exceptional care must be exercised while using these instruments to prevent injury to the patient and/or the surgeon. In particular, the surgeon's hands can be pinched between the hammer portion of the instrument and the hammer stops. Moreover, the size and weight of the slaphammer can make it very difficult for the surgeon to maintain a steady hand. The size and weight can also result in problems with storage and cleaning.

Accordingly, there remains a need for a more compact, lightweight slaphammer device which can be safely and effectively used to apply an impacting force to a medical tool.

SUMMARY OF THE INVENTION

The present invention provides a medical instrument impacting tool which is useful to accurately and safely apply a force to a medical instrument and, in particular, to a tool used during spinal and/or orthopedic surgery. The instrument is designed to provide a safe and accurate procedure for applying a force to a medical device, while minimizing the risk of injury to the patient or to the surgeon's hands during use. The impacting force can be directed to insert or withdraw a medical tool from a location in a patient's body, to prepare an implant site using a broaching device or similar bone preparation device, or to insert an implant between adjacent bone structures. In addition, the compact design of the instrument provides for ease and accuracy of use, as well as ease of cleaning and storage.

In general, the medical instrument impacting tool includes a hollow tube, a mass slidably disposed within the hollow tube, and a handle mated to the mass and slidably movable between a first, distal position and a second, proximal position. The mass, which is slidably disposed within the tube, is mated to the handle such that movement of the handle causes movement of the mass. The instrument also includes a connector element formed on the distal end of the tube and adapted to mate with a medical instrument. The connector element can be, for example, an elongate shaft extending from the distal end of the cylindrical tube and having a T-connector or other similar type of mechanical connector formed on the distal end thereof to mate with a medical instrument.

In one embodiment, the hollow tube includes outer and inner surfaces, a proximal end, and a distal end, and the handle includes a distal end, a proximal end, and a bore formed therein. The handle can be slidably disposed around the hollow tube, or alternatively, it can be positioned proximal to the hollow tube. The tube can be cylindrical and the outer surface of the mass can slidably engage the inner surface of the cylindrical member. This allows the handle to be spaced apart from the cylindrical tube as it travels between the first and second positions. As a result, movement of the mass is only limited by friction between the mass and the tube. The inner diameter of the handle can be greater than the outer diameter of the cylindrical tube. The instrument can also include an elongate rod disposed within the bore of the handle for mating the distal end of the handle to the mass.

In another embodiment, the handle is positioned adjacent to, or along the side of, the hollow tube. A slot extends between the proximal and distal ends of the hollow tube and includes a proximal end and a distal end. A rigid connector element extends through the slot and mates the handle to the mass. The rigid connector element is slidably movable between the proximal and distal ends of the slot.

In other aspects, the instrument can include a first end cap disposed on the distal end of the cylindrical member, and a second end cap disposed on the proximal end of the cylindrical member. The second end cap can include an aperture formed therein for slidably receiving the elongate rod. In use, movement of the handle from the first position to the second position to impact the proximal end of the tube is effective to cause the mass to apply a proximally directed force to the cylindrical tube, and movement of the handle from the second position to the first position to impact the distal end of the tube is effective to cause the mass to apply a distally directed force to the cylindrical tube.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a medical instrument impacting tool that is useful for mating to a medical instrument used during orthopedic surgery. The impacting tool is effective to apply a force to the medical instrument to efficiently and effectively prepare a bone structure, insert or remove an implant, or to remove a medical instrument positioned between adjacent bone structures.

Figure 1:
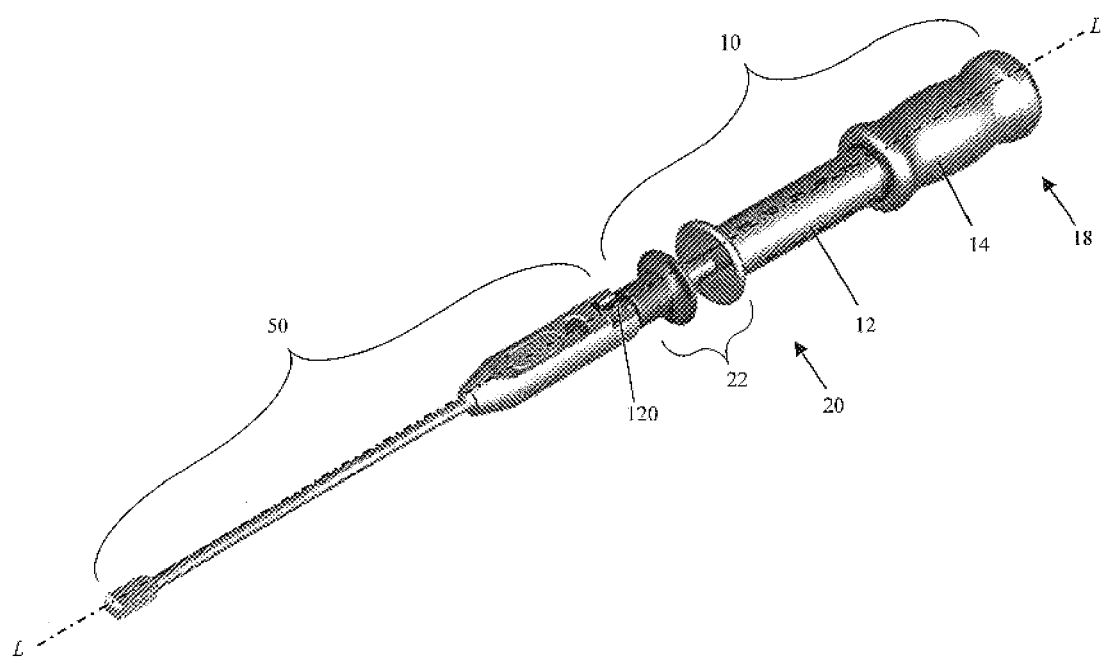
FIG. 1 is a perspective view of a medical instrument impacting tool mated to a medical instrument.
Figure 2:
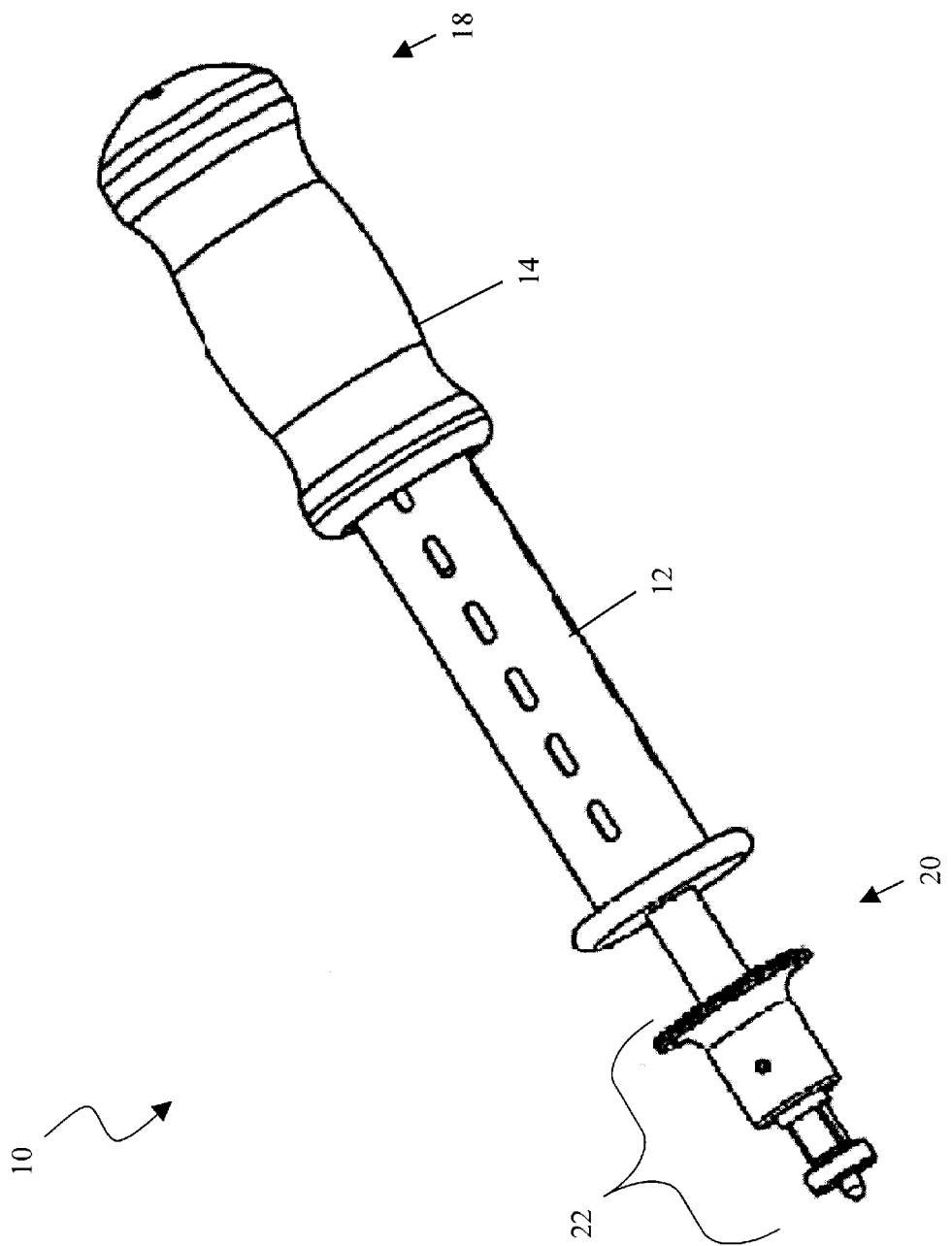
FIG. 2 is a perspective view of the medical instrument impacting tool of FIG. 1 having a hollow cylindrical member, a handle, and a connector element.

As shown in FIGS. 1 and 2, the medical instrument impacting tool 10 generally includes a hollow tube 12, a handle 14 disposed around the tube 12, and a mass 16 (FIG. 6) slidably disposed within the tube 12 and mated to the handle 14. The handle 14 is selectively movable between a first, distal position (not shown) and a second, proximal position (shown in FIGS. 1 and 2), and is effective to move the mass to apply a force to the instrument. The handle 14 and the mass 16 can be used to apply a proximally directed force and/or a distally directed force. The tube 12 includes a proximal end 18, and a distal end 20 adapted to mate with a medical instrument 50, and preferably includes a connector element 22 for removably attaching the impacting tool 10 to the medical instrument 50. FIG. 1 illustrates an exemplary application in which the connector element 22 is mated to a rasp 50, which is effective to remove bone from a bone structure.

Figure 3:
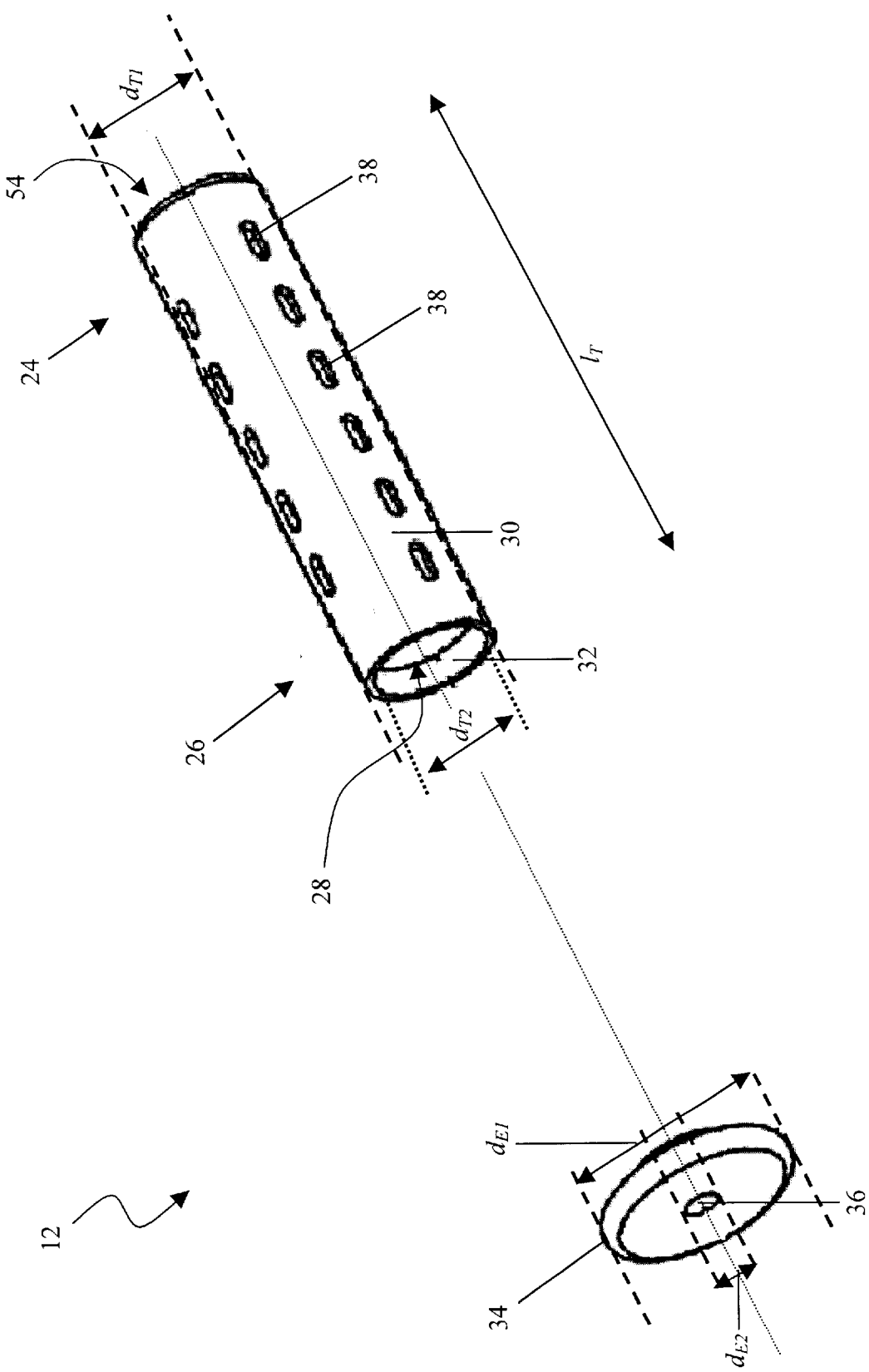
FIG. 3 is a perspective view of the hollow cylindrical member shown in FIG. 2 having an end cap adapted to be disposed on one end of the hollow cylindrical member.

The hollow tube 12 is shown in more detail in FIG. 3, and is generally an elongate rigid tube having a proximal end 24, a distal end 26, and an inner lumen 28 extending therebetween. While the tube 12 is shown having a cylindrical shape, the tube 12 can have any shape and size, such as a square or rectangular shape. The tube 12 includes an outer surface 30, and an inner surface 32, and has an outer diameter $d_{T1}$, a length $l_T$, and an inner diameter $d_{T2}$. The difference between the outer and inner diameters $d_{T1}$, $d_{T2}$ defines the wall thickness of the tube 12, which is generally in the range of about 1 mm to 3 mm, and more preferably is about 1.5 mm. The diameters $d_{T1}$, $d_{T2}$ can vary, but preferably the outer diameter $d_{T1}$ is in the range of about 20 mm to 35 mm, and more preferably is about 25 mm, and the inner diameter $d_{T2}$ is in the range of about 15 to 30 mm, and more preferably is about 22 mm. The length of the tube $l_T$ can also vary, but should be sufficient to allow the mass 16 to slidably move between the proximal and distal ends 24, 26 of the tube 12, and to apply a sufficient force to the tube 12. Preferably, the length $l_T$ is in the range of about 80 mm to 130 mm, and more preferably about 105 mm.

The cylindrical tube 12 can optionally include a plurality of air flow openings 38 extending from the outer surface 30 to the inner surface 32. The openings 38 are effective to prevent the buildup of pressure within the cylindrical tube 12, and thus they are effective to allow the mass to slide freely between the proximal and distal ends 24, 26 of the tube 12. In addition, the openings facilitate cleaning of the instruments. The openings 38 can have any shape and size, and can be formed anywhere along the length $L_T$ of the tube 12. As shown in FIG. 3, the openings 38 are spaced apart and formed in rows extending from the proximal end 24 to the distal end 26 of the tube 12.

The proximal and/or distal ends 24, 26 of the cylindrical tube 12 can include an end surface 54 (shown in FIG. 6 adapted to mate to the proximal end 24 of the tube 12) formed integrally with the cylindrical tube 12. Alternatively, the proximal and/or distal end 24, 26 of the cylindrical tube 12 can include an end cap fixedly attached to or removably disposed thereon. FIG. 3 illustrates an end cap 34 adapted to be disposed on the distal end 26 of the tube 12. The end cap 34 can be fixedly attached to or removably matable to the cylindrical member 12 using a variety of attachment mechanisms. For example, the end cap 34 can be welded, adhesively secured, or mechanically connected (e.g., by threads) to the cylindrical tube 12. Where the end cap 34 is to be removably mated to the cylindrical tube 12, the outer perimeter of the end cap 34 can include, for example, threads (not shown) formed thereon, and the inner perimeter of the cylindrical member 12 can include corresponding threaded grooves (not shown) formed therein and adapted to threadingly receive the end cap 34. A person having ordinary skill in the art will appreciate that other mating elements can be used to attach the end cap 34 to the cylindrical member 12.

The end cap 34 can be adapted to fit within the tube 12, to be disposed on the end of the tube 12, or to extend radially outward from the end of the tube 12. Thus, the end cap 34 can have an outer diameter $d_{E1}$ slightly less than as the inner diameter $d_{T2}$ of the tube 12, equal to the inner diameter $d_{T2}$ or outer diameter $d_{T1}$ of the tube 12, or greater than the outer diameter $d_{T1}$ of the tube 12. In an exemplary embodiment, the end cap 34 has an outer diameter $d_{E1}$ substantially greater than the outer diameter $d_{T1}$ of the tube 12. As a result, the end cap 34 forms an annular flange extending radially outward from the tube 12. The end cap 34 can optionally include a bore 36 disposed partially or entirely therethrough.

Where the end cap 34 is disposed on the distal end 26 of the tube, the bore 36 is adapted to mate to a portion of the connector element 22. Preferably, the bore 36 is threaded to receive a corresponding threaded member on the connector element 22, which will be described in more detail with reference to FIG. 7. Where the end cap 34 is disposed on the proximal end 24 of the tube 12, the bore 34 (FIG. 6) is adapted to receive an elongate rod 80 (FIG. 4) which is effective to mate the handle 14 to the mass 16. The elongate rod will be described in more detail with reference to FIG.

4. The diameter $d_{E2}$ of the bore 36 can vary, but is preferably in the range of about 2 mm to 12 mm, and more preferably is in the range of about 6–8 mm. In an exemplary embodiment, shown in FIG. 7, the distal end 26 of the cylindrical member includes an end cap 34 having a bore 36 formed therein and having an outer diameter $d_{E1}$ greater than the outer diameter $d_{T1}$ of the cylindrical tube 12, and the proximal end 24 includes an end surface 54 formed integrally with the cylindrical member 12 and also having a bore 56 (FIG. 6) formed therein. The bore 56 in the end surface 54 preferably has a diameter in the range of about 2 mm to 10 mm, and more preferably about 6 mm.

Figure 4:
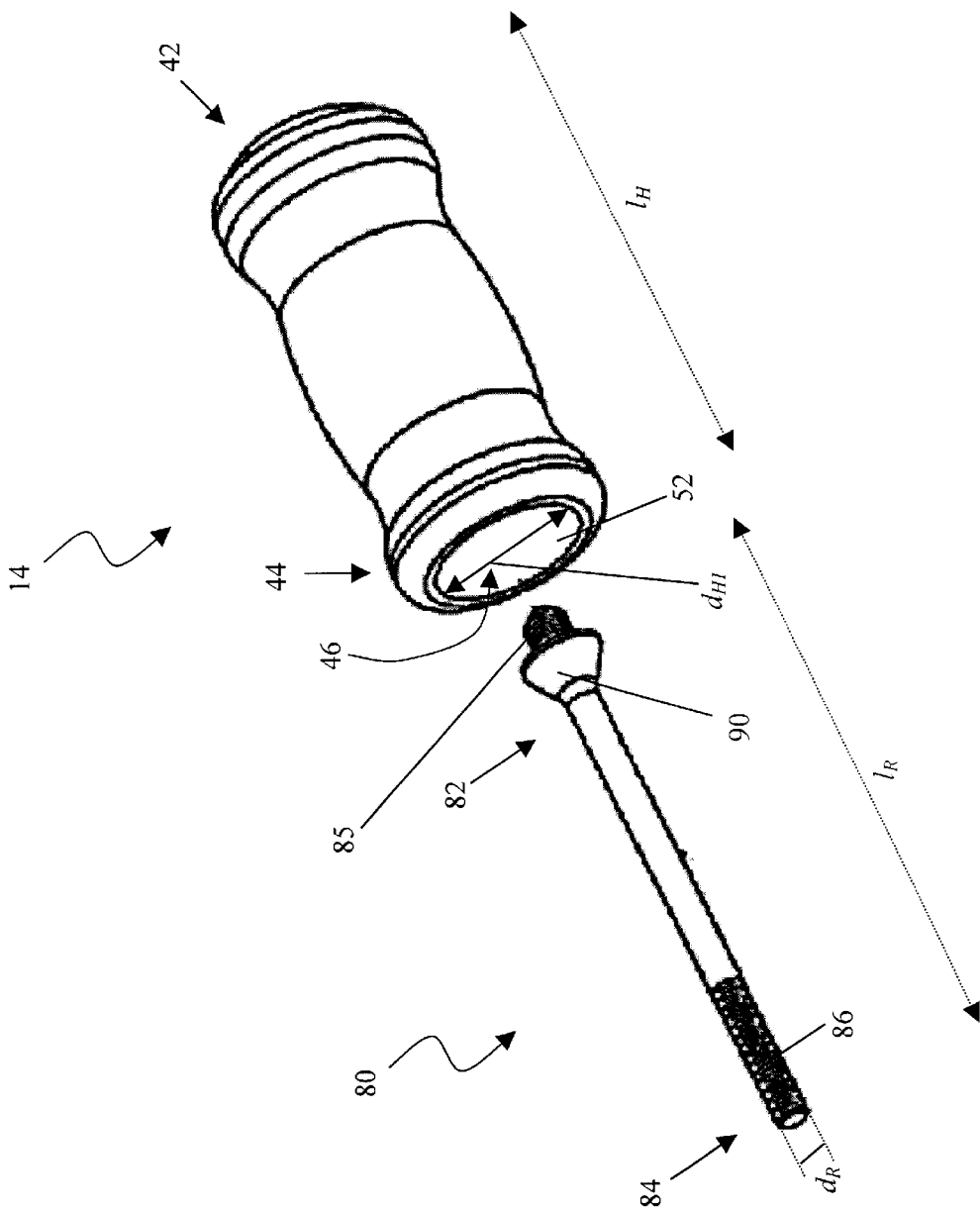
FIG. 4 is a perspective view of the handle of the tool shown in FIG. 2 having an elongate rod adapted to mate the handle to a slidable mass.

The handle 14 of the tool 10 is shown in FIG. 4, and is adapted to be slidably disposed around the tube 12. In use, the handle 14 is movable between a first, distal position (not shown), and a second, proximal position (shown in FIG. 1). The handle 14 can have a variety of different shapes and sizes, but is preferably generally cylindrical and includes a proximal end 42, a distal end 44, and a bore 46 extending there between. A person having ordinary skill in the art will appreciate that the handle can have a shape that conforms to the shape of the tube 12, such as square or oval, or can have a suitable alternative shape.

The outer surface of the handle 14 can be shaped to facilitate grasping of the handle 14 during use, and can optionally include a textured surface to facilitate manual movement of the handle 14. The inner surface 52 of the handle 14 defines the bore 46, which has a diameter $d_{H1}$ that is about same as, or preferably greater than, the outer diameter $d_{T1}$ of the cylindrical tube 12. The diameter $d_{H1}$ of the bore 46 is preferably in the range of about 20 to 35 mm, and more preferably is about 28 mm. In one embodiment, the handle 14 is adapted to fit around the cylindrical tube 12, yet the inner surface 52 is spaced apart from the tube 12 such that, during use, the handle 14 does not come into contact with the cylindrical tube 12. The proximal inner end surface 98 (FIG. 6) of the handle 14 can, however, come into contact with the proximal end surface 54 of the cylindrical tube 12 when the handle 14 is positioned in the first, distal position wherein the handle 14 is substantially or fully disposed around the cylindrical tube 12. In an exemplary embodiment, the handle 14 does not come into any physical contact with the cylindrical tube 12 during use.

The handle 14 is adapted to mate with the mass 16, and thus can include an elongate rod 80 disposed therein, having proximal end 82 matable with the handle 14 and a distal end 84 matable with the mass 16. The elongate rod 80 can have any shape, such as cylindrical, square, and the like, but is preferably a solid circumferential rod having a diameter $d_R$ substantially less than the diameter $d_{H1}$ of the bore 46 in the handle 14. The rod 80 should be adapted to be slidably disposed through the bore 56 in the proximal end surface 54 of the cylindrical member 12, shown in FIG. 6, and thus should have a diameter $d_R$ slightly less than the diameter of the bore 56. The length $l_R$ of the rod 80 should be about the same as, or greater than, the length $l_H$ of the handle 14, and should be adapted to allow the mass 16 to contact and move between the distal inner most surface 125 (FIG. 6) of the tube 12, e.g. the end cap 34, and the proximal most inner end surface 54 of the tube 12. Moreover, the length $l_R$ of the rod 80 is preferably adapted to prevent the handle 14 from contacting the cylindrical tube 12 when moved to the distal position (not shown). In an exemplary embodiment, the diameter $d_R$ of the rod 80 is in the range of about 3 mm to 10 mm, and more preferably is about 6 mm, and the length $l_R$ of the rod 80 is in the range of about 100 mm to 140 mm, and more preferably is about 120 mm.

Figure 5:
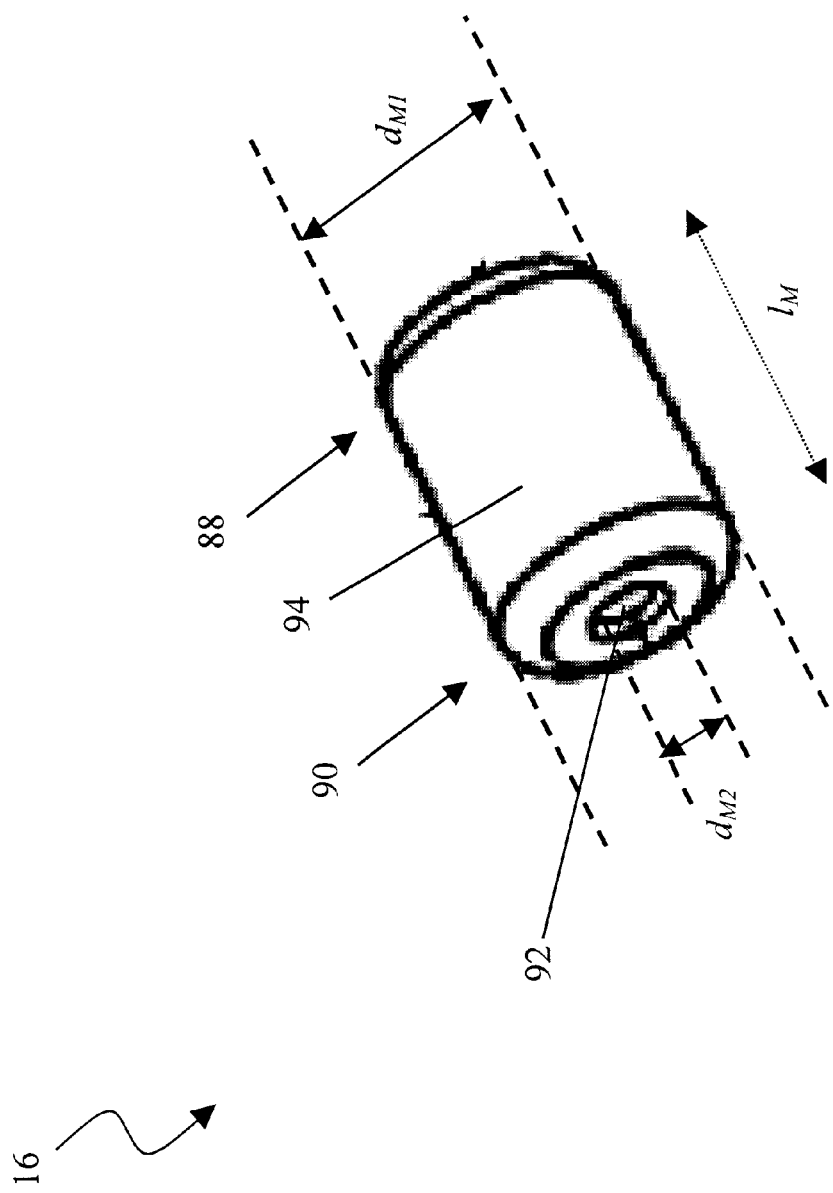
FIG. 5 is a perspective view of a slidable mass adapted to be disposed within the hollow cylindrical member of FIG. 3 and adapted to mate to the handle shown in FIG. 4.

Still referring to FIG. 4, the proximal end 82 of the rod 80 can include threads 85 for mating with a corresponding threaded bore (not shown) formed in the inner proximal end 98 (FIG. 6) of the handle 14. The distal end 84 of the rod 80 can also include threads 86 for mating with a corresponding threaded bore (not shown) formed in the proximal end 88 of the mass 16 (FIG. 5). While threads 85, 86 are shown, the rod 80 can be fixedly attached to the handle 14 and/or the mass 16. Alternatively, virtually any other type of connecting mechanism can be used to mate the rod 80 to the handle 14 and/or the mass 16. The rod can optionally include an annular protrusion 90 formed on the proximal end 82 of the rod 80 and having a flattened proximal end surface (not shown) which is adapted to abut the inner proximal end surface 98 of the handle 14. The annular protrusion 90 is effective to ensure that the rod 80 is axially aligned with the longitudinal axis L of the instrument 10.

The mass 16 is shown in FIG. 5, and is adapted to mate to the distal end 84 of the elongate rod 80, and to be slidably disposed within the cylindrical tube 12. The mass 16 can have a variety of shapes, but should have a shape substantially the same as the shape of the inner surface 32 of the tube 12. As shown, the mass 16 has a generally cylindrical shape and includes a proximal end 88, a distal end 90, and, optionally, a bore 92 extending therebetween. The bore is preferably formed along the longitudinal axis L of the instrument 10, such that the mass is disposed along the center of gravity of the instrument. The bore 92 can include threads (not shown) for receiving the threaded distal end 84 of the rod 80. The diameter $d_{M2}$ of the bore 92 should be substantially the same as, but slightly larger than the diameter $d_R$ of the rod 80, and is preferably in the range of about 3 mm to 10 mm, and more preferably is about 6 mm. The mass 16, however, can be a solid cylindrical member, and the elongate rod 80 can be formed integrally with the mass 16, or it can be fixedly attached to the mass 16.

The mass 16 includes an outer surface 94 which defines a diameter $d_{M1}$. The outer surface 94 of the mass 16 is preferably adapted to engage the inner surface 32 of the cylindrical tube 12, and thus should have a diameter $d_{M1}$ slightly less than the inner diameter $d_{T2}$ of the tube 12. The engaging fit between the mass 16 and the cylindrical tube 12 allows the handle 14 to be slidably disposed around, yet spaced apart from, the cylindrical tube 12, thereby eliminating any friction between the handle 14 and the tube 12. While the diameter $d_{M1}$ of the mass 16 can vary as long as the diameter $d_{M1}$ is less than the inner diameter $d_{T2}$ of the tube 12, the diameter $d_{M1}$ is preferably between about 15 mm to 30 mm, and more preferably about 21 mm. The mass also includes a length $l_M$, which can vary, but is preferably adapted to allow the mass 16 to move between the proximal and distal ends 24, 26 of the cylindrical tube 12. Thus, the length $l_M$ of the mass 16 should be substantially less than the length $l_T$ of the tube 12, and is preferably in the range of about 20 mm to 40 mm, and more preferably is about 29 mm. Moreover, the mass 16 should have a weight sufficient to allow the mass 16 to apply a force to the instrument 10, the force being effective to move the instrument 10 in a desired direction.

Figure 6:
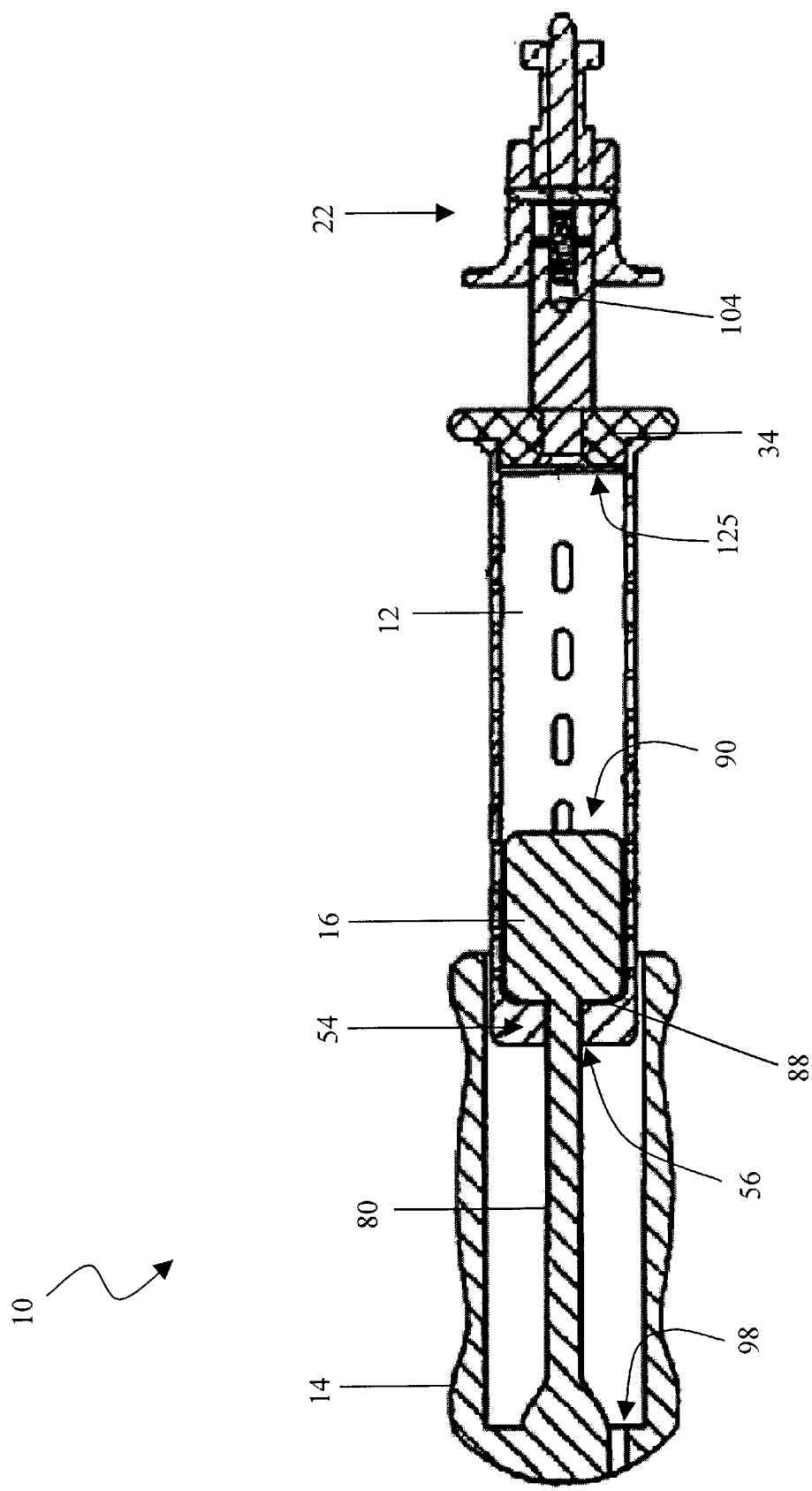
FIG. 6 is a cross-sectional illustration of the all of the components of the medical instrument impacting tool shown in FIG. 2 in the assembled form.

FIG. 6 illustrates the impacting tool 10 in the assembled form. While the tool 10 is shown fully assembly, each of the components of the tool 10 can be fixedly attached or alternatively can be disassembled to allow the instrument to be sterilized and/or stored prior to each use. As shown, the mass 16 is slidably disposed within the cylindrical tube 12 and engages the inner wall 32 of the tube 12. The proximal end of the mass is mated to the elongate rod 80, which is attached to the proximal inner end surface 98 of the handle 14. The elongate rod 80 is slidably disposed through the bore 56 formed in the proximal end 24 of the cylindrical tube 12.

In use, the handle 14, and consequently the elongate rod 80 and the mass 16, are slidably movable between a first, distal position (not shown) wherein the distal end 90 of the mass 16 is in contact with the inner distal end surface of the cylindrical tube 12, e.g. the end cap 34, and a second, proximal position as shown wherein the proximal end 88 of the mass 16 is in contact with the inner proximal end surface 54 of the cylindrical tube 12. Movement of the handle 16 is effective to move the mass 16, and, upon impact with the end cap 34 and/or end surface 54, apply a force to the cylindrical tube 12. Thus, to move the instrument 10 in a distal direction, the handle 14 can be moved from the second, proximal position to the first, distal position to cause the mass 16 to impact the end cap 34 of the cylindrical tube 12, thereby applying a distally directed force to the instrument 10. The handle 14 can be used to apply both a proximally directed force and a distally directed force to the instrument 10, and thereby apply a force to the medical device 50 attached to the instrument.

Figure 8A:
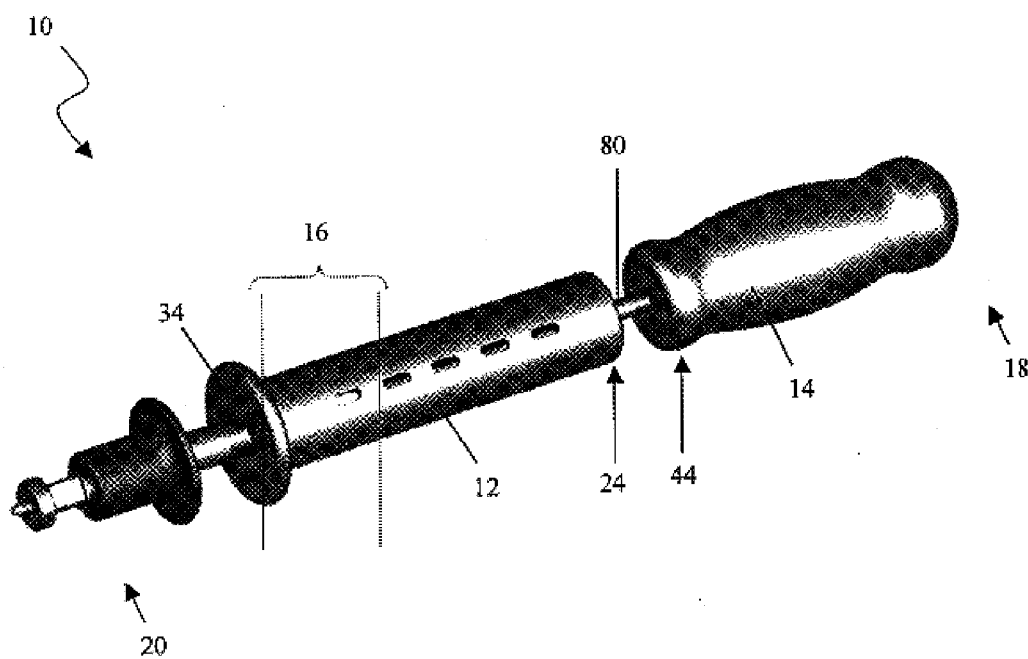
FIG. 8A is a perspective view of another embodiment of a medical instrument shown in a distal position and having the handle positioned proximal to the hollow cylindrical tube.
Figure 8B:
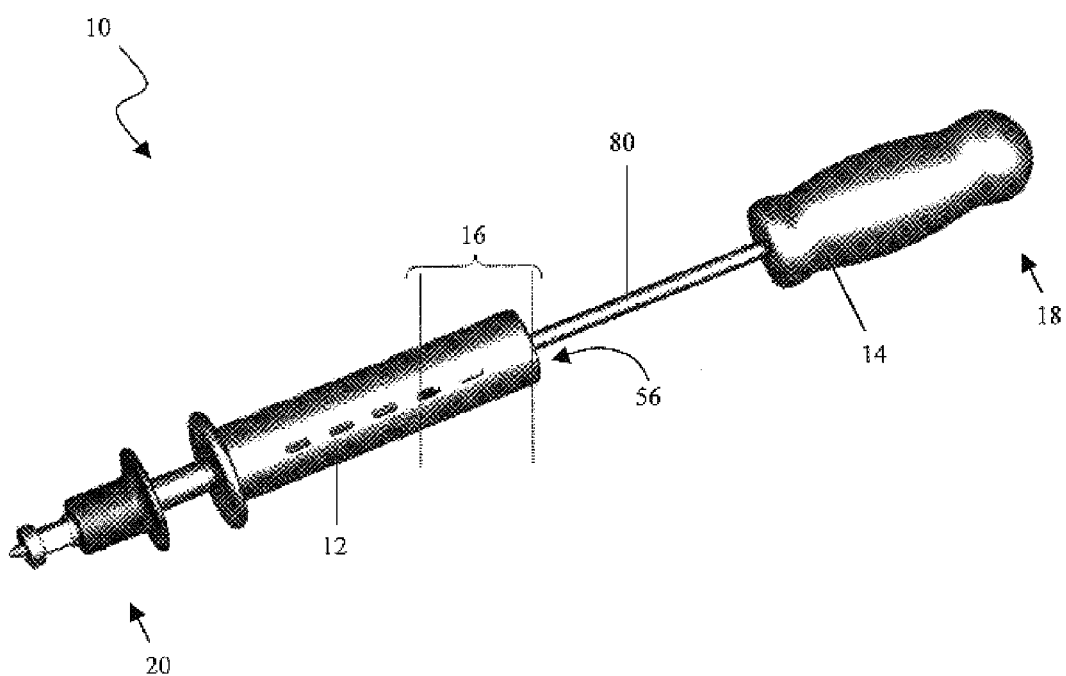
FIG. 8B is a perspective view of the medical instrument of FIG. 8A shown in a proximal position.
Figure 9:
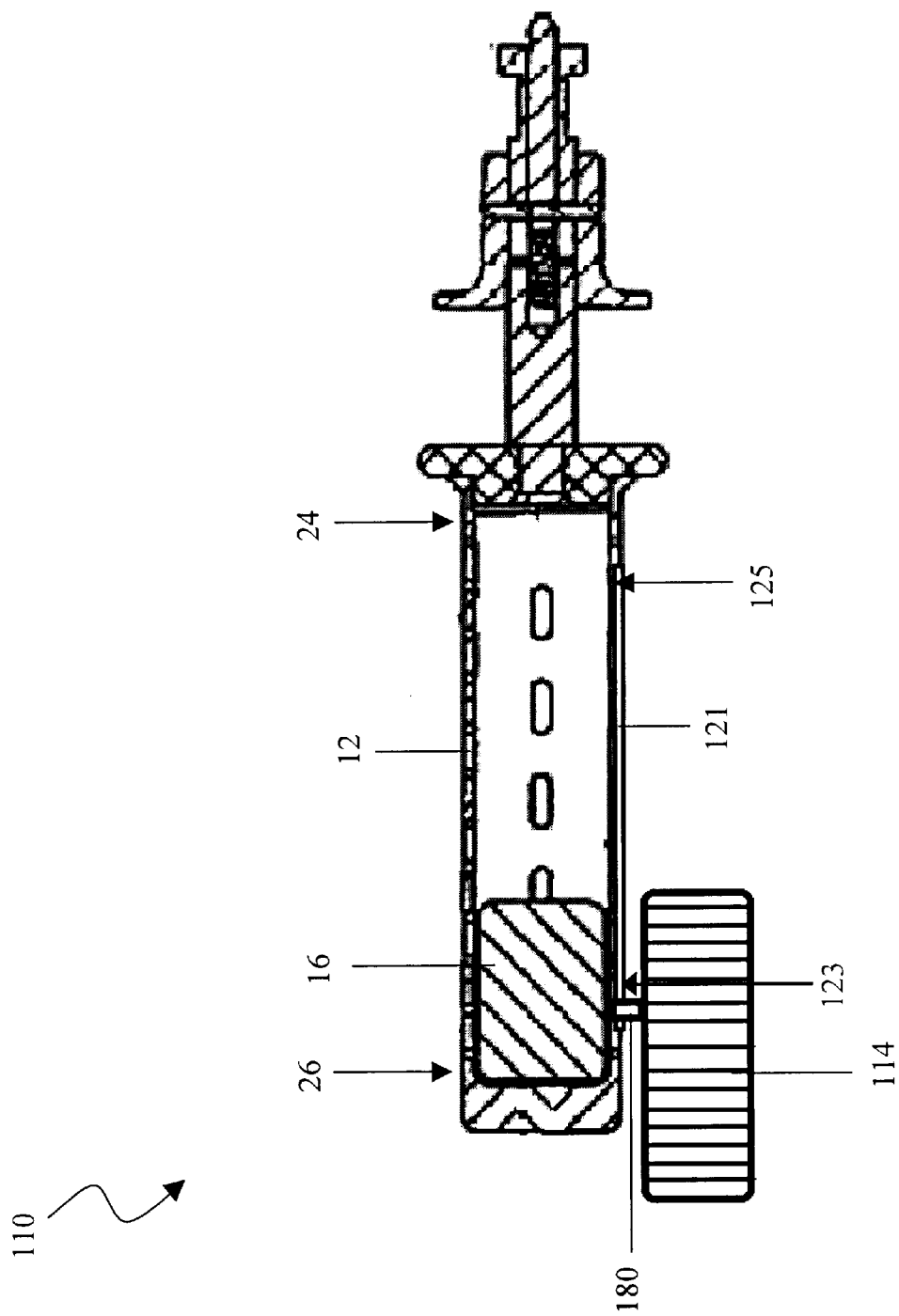
FIG. 9 illustrates yet another embodiment of the medical instrument having a handle disposed adjacent to the hollow cylindrical member.

A person having ordinary skill in the art will appreciate that the medical instrument 10 can have a variety of configurations. For example, the handle 14 can also be disposed around a portion of the tube, positioned along one side of the tube 12, or positioned proximal to the tube. FIGS. 8A and 8B illustrate one embodiment wherein the handle 14 is disposed proximal to the proximal end 24 of the tube 12. FIG. 8A illustrates that handle 14 in the distal position. As shown, the mass 16 is in contact with the end cap 34, and the distal end 44 of the handle 14 does not come into contact with the proximal end 24 of the tube 12. FIG. 8B illustrates the handle 14 in the proximal position, wherein the mass 16 is in contact with the end surface 56 of the tube 12, and the elongate rod 80 is fully extended from the tube 12. FIG. 9 illustrates another embodiment of a medical instrument 110 having a handle 114 disposed adjacent to, or along the side of, the tube 12. A rigid connector element 180 extends from the handle 114 through a slot 121 formed along the length of the tube 12 to connect the handle 114 to the mass 16. The slot 121 extends between the proximal and distal ends 24, 26 of the tube 12, and includes a proximal end 123 and a distal end 125. The rigid connector element 180 can have virtually any shape, but should be adapted to slidably move between the proximal and distal ends 123, 125 of the slot 121.

Figure 7:
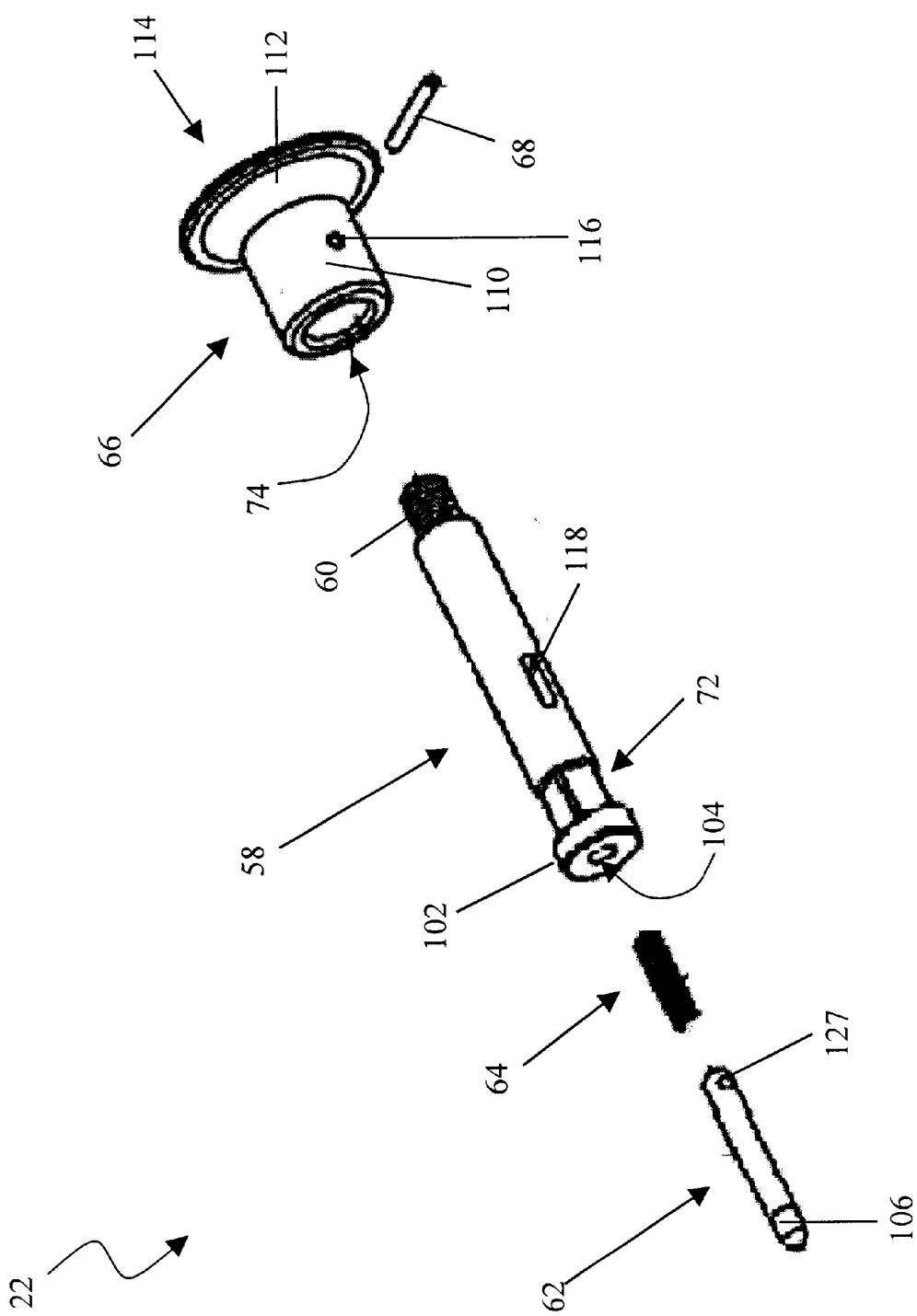
FIG. 7 is a perspective view of the components of one embodiment of the connecting element of the tool shown in FIG. 2 in a disassembled form.

Referring back to FIG. 1, the instrument 10 includes a connector element 22 adapted to mate to a medical device 50. The instrument 10 can be used with a variety of medical devices, and thus can include virtually any type of connector element effective to mate to the desired medical device. FIG. 7 illustrates an exemplary embodiment of a connector element 22, which is adapted to mate to the distal end 26, or more specifically the end cap 34, of the elongate cylindrical tube 12. The connector element 22 includes a mating rod 58 having a threaded proximal end 60 and a distal end 72, a flange 66 having an inner lumen 74 formed therein and adapted to receive the mating rod 58, a connector pin 62, a biasing element 64, and a locking element 68.

The flange 66 includes a cylindrical portion 110 and a radial flange portion 112 located on the proximal end 114. An inner lumen 74 extends through the cylindrical portion 110 and the radial flange 112, and is adapted to receive the mating rod 58, which is preferably fully disposed through the inner lumen 74 of the flange 66 such that the mating rod 58 extends from the flange 66 in both the proximal and distal directions.

The mating rod 58 includes a threaded proximal end 60 adapted to mate with the threaded bore 36 formed in the end cap 34 on the distal end 26 of the cylindrical tube 12, and a distal end 72 having a T-connector 102 formed thereon and adapted to mate with a corresponding T-shaped groove 120 formed in the medical instrument 50 (FIG. 1). The T-connector 102 includes a bore 104 extending from the distal end 72 to approximately the middle of the mating rod 58, as shown in FIG. 6. The bore 104 is adapted to receive the biasing element 64 and the connector pin 62. The biasing element 64 can be, for example, a spring or similar device. In use, the pin 62 is disposed within the bore 104, and includes a distally protruding tip 106. The biasing element 64, which is disposed proximal to the pin 62, is effective to provide a biasing force against the connector pin 62 when the distally protruding tip 106 is fully inserted into the bore 104.

The connector element can include a locking element 68, e.g. a pin member, which is effective to secure the flange 66 to the mating rod 58, and to retain the connector pin 62 within the bore 104 in the mating rod 58. The locking element 68 is adapted to be disposed through a transverse bore 116 in the flange 66, a slot 118 in the mating rod 58, and a transverse bore 127 in the connector pin 62. The elongate slot 58 allows the connector pin 62 to be moved between a first, extended position wherein the distal tip 106 extends from the bore 104 in the mating rod, and a second, retracted position wherein the distal tip 106 is fully disposed within the bore 104.

Referring back to FIG. 1, the connector element 22 is shown mated to a medical instrument 50. The medical instrument, e.g. a rasp, includes a T-shaped slot 120 which is adapted to receive the T-connector 102 of the mating rod 58. Prior to insertion of the T-connector 102 into the slot 120, the connector pin 62 is positioned in the second, retracted position. The flange 66 can be moved proximally to move the connector pin 62 from the first position to the and second position. Once the T-connector 102 is inserted into the T-shaped slot 120, the biasing element 64 causes the connector pin 62 to return to the first, extended position, wherein the distal tip 106 is disposed within an inner bore (not shown) formed in the medical instrument 50. The connector pin 62 prevents the medical instrument 50 from detaching from the impacting tool 10 during use. Once attached, the impacting device 10 can be used to apply either a proximally directed force or a distally directed force to the medical device 50. As shown in FIG. 1, the medical device is a rasp, thus the impacting device 10 can be used to apply a distally directed force to the rasp 50 to remove bone from a bone structure.

Although the invention is described with reference to use with a rasp, any type of broaching device can be used. In addition, it is understood that the impacting tool of the invention can be used with virtually any medical instrument having any configuration, especially those used during joint or spinal surgery. For example, the impacting tool can be used with prosthesis placement tools, bone preparation instruments, implant removal tools, spreader devices, and the like. Exemplary medical instruments includes chisels, rasps, broaches, saws, spreaders, and trial implants. Moreover, while a T-connector is illustrated, a person having ordinary skill in the art will appreciate that a virtually any type of connector element can be provided. By way of non-limiting example, the connector can employ a threading engagement, a snapping engagement, a frictional fit, a rotational fit, a push-button connector, a J-type connector, or any other type of mating member.

While the medical instrument of the invention is generally described as being adapted to apply a proximally or distally directed force to a medical tool, the medical instrument can optionally be adapted to provide some other type of movement, such as, for example, rotational or vibrational movement. Moreover, the components of the medical instrument can be rotationally mated to each other.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical instrument impacting tool, comprising:
   a hollow tube having inner and outer surfaces, a proximal end, and a distal end, the distal end including a connector element adapted to mate with a medical device;
   a handle having a bore extending therein from a distal end to a proximal end thereof, the handle being slidably disposed around the tube such that it is able to move selectively between a first, distal position and a second, proximal position; and
   a mass slidably disposed within the hollow tube and having a proximal end and a distal end, the mass being connected to the handle such that proximal movement of the handle causes simultaneous movement of the mass in a proximal direction to deliver a proximally directed force, and distal movement of the handle causes simultaneous movement of the mass in a distal direction to deliver a distally directed force.

2. The medical instrument impacting tool of claim 1, wherein an outer surface of the mass slidably engages the inner surface of the hollow tube.

3. The medical instrument impacting tool of claim 2, wherein the hollow tube is a cylindrical tube and the bore of the handle has an inner diameter greater than an outer diameter of the cylindrical tube such that the handle is disposed around, but spaced apart from the cylindrical tube as it travels between the first and second positions.

4. The medical instrument impacting tool of claim 2, further comprising an elongate rod disposed within the bore of the handle and extending from the distal end of the handle to the mass.

5. The medical instrument impacting tool of claim 4, further comprising a first end cap disposed on the distal end of the cylindrical member, and a second end cap disposed on the proximal end of the cylindrical member, the second end cap including a bore formed therein for slidably receiving the elongate rod.

6. The medical instrument impacting tool of claim 5, wherein the mass is effective to apply a proximally directed force to the cylindrical member and the proximal end cap is effective to receive the proximally directed force from the mass upon movement of the handle from the first position to the second position, and the mass is effective to apply a distally directed force to the cylindrical member and the distal end cap is effective to receive the distally directed force from the mass upon movement of the handle from the second position to the first position.

7. A tool for impacting a medical instrument used during surgery, comprising:
   an elongate body having a proximal portion, a distal portion, and an inner lumen formed therein, the distal portion including a connector element adapted to mate with a medical instrument;
   a grasping element having a bore extending therein from a distal end to a proximal end thereof, the grasping element being slidably disposed around the elongate body and selectively movable between a first position and a second position; and
   a slidable weight disposed within the inner lumen of the elongate body and effective to apply proximally and distally directed forces to the elongate body, the slidable weight being mated to the grasping element such that proximal movement of the grasping element causes simultaneous movement of the slidable weight in a proximal direction and a distal movement of the grasping element causes simultaneous movement of the slidable weight in a distal direction.

8. The tool of claim 7, wherein an outer surface of the weight slidably engages an inner surface of the inner lumen of the elongate body.

9. The tool of claim 8, wherein movement of the grasping element from the first position to the second position is effective to cause the slidable weight to apply a force to the tool, the force being sufficient to move the elongate body.

10. The tool of claim 9, wherein the bore of the grasping element has an inner diameter greater than an outer diameter of the elongate body such that the grasping element is disposed around and spaced apart from the elongate body.

11. The tool of claim 10, wherein the slidable weight and the grasping element can be locked in at least one of the first and second positions.

12. The tool of claim 11, wherein the elongate body includes a proximal end surface, movement of the grasping element in a proximal direction being effective to cause the slidable weight to abut the end surface of the elongate body thereby creating a proximally directed force.

13. The tool of claim 11, wherein the elongate body includes a distal end surface, movement of the grasping element in a distal direction being effective to cause the slidable weight to abut the end surface of the elongate body thereby creating a distally directed force.

14. The tool of claim 12, wherein the connector element comprises an elongate shaft extending from the distal end of the elongate body, a distal end of the connector element having a T-connector able to selectively connect to a medical instrument.

15. A medical instrument impacting tool, comprising:
   a hollow tube having inner and outer surfaces, a proximal end, and a distal end, the distal end including a connector element adapted to mate with a medical device;
   a mass slidably disposed within the hollow tube and having a proximal end and a distal end, the mass being effective to apply proximally and distally directed forces to the hollow tube; and
   a handle mated to the mass and being selectively movable between a first, distal position and a second, proximal position, such that movement of the handle causes simultaneous movement of the mass.

16. The medical instrument of claim 15, wherein the handle is positioned proximal to the hollow tube in both the first and second positions, and wherein the mass is positioned adjacent to the distal end of the hollow tube in the first, distal position, and adjacent to the proximal end of the hollow tube in the second position.

17. The medical instrument of claim 16, further comprising an elongate rod extending from a distal end of the handle to the proximal end of the mass.

18. The medical instrument of claim 15, wherein the handle is positioned adjacent to the outer surface of the hollow tube.

19. The medical instrument of claim 18, wherein the hollow tube includes an elongate slot extending between the proximal and distal ends of the tube, and the instrument further includes a rigid connector element extending from the handle through the elongate slot to the mass, the rigid connector element being movable between a proximal end and a distal end of the elongate slot.

* * * * *